United States Patent [19]

Squire

[11] 4,431,786

[45] Feb. 14, 1984

[54] NOVEL FLUORODIOXOLES AND FLUORODIOXOLE POLYMERS

[75] Inventor: Edward N. Squire, Glen Mills, Pa.

[73] Assignee: E. I. Du Pont de Nemours and Company, Wilmington, Del.

[21] Appl. No.: 375,468

[22] Filed: May 6, 1982

[51] Int. Cl.³ .............................................. C08F 14/18
[52] U.S. Cl. .................................................... 526/247
[58] Field of Search ......................................... 526/247

[56] References Cited

U.S. PATENT DOCUMENTS 3,308,107  3/1967  Selman et al. ...................... 526/247
3,978,030  8/1976  Resnick ............................... 526/247

Primary Examiner—Harry Wong, Jr.

[57] ABSTRACT

Novel fluorodioxoles which may have Cl or F substituents in the 4 or 5 positions and have two F or CF₃ substituents in the 2 position are useful monomers for the preparation of homopolymers and copolymers with tetrafluoroethylene and terpolymers with tetrafluoroethylene and vinylidene fluoride. The homopolymers are suitable for glazing materials, while copolymers are useful, among others, for corrosion-resistant seals, gaskets, and linings.

9 Claims, No Drawings

NOVEL FLUORODIOXOLES AND FLUORODIOXOLE POLYMERS

BACKGROUND OF THE INVENTION

This invention relates to certain novel fluorodioxoles, their polymers, and processes for making the fluorodioxoles.

Various dioxolanes having the following formula 1 are known from German Patent No. 2,604,350 to Stanford Research Institute:

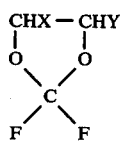  (1)

where each of X and Y may be F or Cl.

Dioxolanes corresponding to formula (2), below, are reported in U.S. Pat. No. 3,749,791 to Terrell et al.:

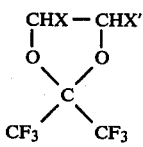  (2)

where X is Cl or F, and X' is H, Cl, or F.

The intermediate 2,2-bis(trifluoromethyl)-1,3-dioxolane is known from U.S. Pat. No. 2,925,424 to Simmons.

Dechlorination of 2,2-bis(trifluoromethyl)-4,5-dichloro-4,5-difluoro-1,3-dioxolane to the corresponding perfluorodioxole has been reported by Resnick in U.S. Pat. Nos. 3,865,845 and 3,978,030.

That perfluorodioxole has been found to form both homopolymers and copolymers (especially with tetrafluoroethylene) which have interesting chemical and physical properties (e.g., chemical inertness to hydrogen fluoride, optical clarity, ability to form films). It can be speculated that simpler and/or cheaper fluorodioxoles also would be capable of forming useful homopolymers and copolymers.

SUMMARY OF THE INVENTION

According to the present invention, there is provided a class of fluorodioxoles having the following formula (3):

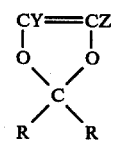  (3)

in which Y is hydrogen or chlorine; Z is hydrogen, fluorine, or chlorine; and R is fluorine or the trifluoromethyl group; with the proviso that when R is trifluoromethyl, only one of Y and Z can be hydrogen or chlorine.

These fluorodioxoles are useful monomers for the preparation of homopolymers and copolymers having a wide range of potential applications. This invention also includes such polymers as well as certain novel polymers of known dioxoles. Generally, the monomers from which the novel polymers of the present invention are made can be represented by the same formula (3) in which Y, Z and R have the same meaning as above, but the above proviso no longer applies.

DETAILED DESCRIPTION OF THE INVENTION

The fluorodioxoles of the present invention can be conveniently made by dechlorination of the corresponding 4,5-dichlorodioxolanes with magnesium in the presence of a catalytic amount of iodine and of a water-soluble mercury salt or metallic mercury, as shown in the following equation.

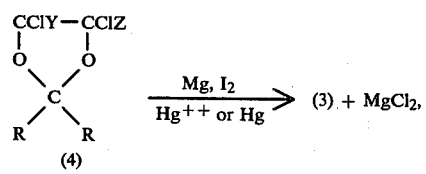

Where R, Y, and Z have the same meaning as in Formula (3), above.

This dechlorination reaction preferably is carried out in solution in tetrahydrofuran. For maximum production rate, an excess of magnesium is employed in this reaction, the preferred amount being 1.1 to 8 gram-atoms of magnesium per two gram-atoms of vicinal chlorine to be removed. However, for maximum yield of dioxole, less than stoichiometric amounts may be desirable to minimize side reactions. Mercury salts suitable in this reaction include, for example, mercuric chloride, acetate, and nitrate. Metallic mercury, when used, forms in situ an amalgam with magnesium. However, an amalgam can be prepared separately in advance. The amount of mercury need not be large. For example, a weight of mercuric chloride about equal to the weight of iodine, in turn equal to about 1% of the weight of magnesium usually is sufficient. A slightly larger amount of metallic mercury may be advisable to permit more effective agitation and thus easier amalgam formation.

Although some 4,5-dioxolanes represented by the above formula (4) are known, as discussed earlier, those represented by formula (5), below are believed to be novel:

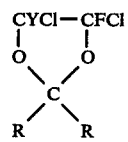  (5)

in which R is fluorine or trifluoromethyl, and Y is hydrogen or chlorine.

All the fluorodioxoles of this invention copolymerize with tetrafluoroethylene (TFE) to tough, crystalline copolymers suitable for use as a dielectric in electrical and electronic equipment. In these crystalline copolymers the fluorodioxole usually is present in an amount of about 12 mole percent or less. When the fluorodioxole content increases beyond 12 mole percent, the copolymers become amorphous. Naturally, the 12 mole percent level is not a sharp line of demarcation, since copolymers having some crystallinity may exist above it, and significantly amorphous copolymer may exist below it. However, one can expect that a large majority of copolymers having less than 12 mole % of a fluorodioxole (3) will be crystalline, and a large majority of those containing more than 12 mole % of such a fluorodioxole will be amorphous. The amorphous copolymers are tough and at moderate molecular weight soluble in various organic liquids, such as 1,1,2-trichloro-1,2,2-trifluoroethane and "Fluorinert" Electronic Liquid FC-75 (3M Company) and are particularly suitable for finishes and coatings that are chemically inert and are stain and weather resistant. Fluorodioxoles (3) in which each of Y and Z is chlorine could not be incorporated into a copolymer with TFE at a high enough level to result in an amorphous copolymer. Those copolymers that were made were crystalline.

Fluorodioxoles (3) form with vinylidene fluoride ($VF_2$) and TFE strong, plastic and elastomeric terpolymers suitable for corrosion-resistant seals, gaskets, and linings.

Finally, the fluorodioxoles corresponding to formula (3) in which Y is hydrogen and Z is hydrogen or fluorine form homopolymers, which are tough, amorphous resins suitable for transparent glazing materials, especially as sight glasses in chemically corrosive uses employing hydrogen fluoride.

In addition to the novel dioxoles of Formula 3 as defined therein, dioxoles in which both X and Y are hydrogen or chlorine, and R is trifluoromethyl can be made by the same general techniques but are not believed to be novel. Those dioxoles also form novel and valuable copolymers; the dioxoles in which X is hydrogen, and Y is hydrogen or fluorine also form homopolymers.

Broadly, this invention includes, therefore, homopolymers of the novel dioxoles of this invention as well as copolymers of the dioxoles represented by formula (3) in which Y is hydrogen or chlorine; Z is hydrogen, fluorine, or chlorine; and R is fluorine or trifluoromethyl with tetrafluoroethylene and terpolymers with tetrafluoroethylene and vinylidene fluoride.

This invention is now illustrated by representative examples of certain preferred embodiments thereof, wherein all parts, proportions, and percentages are by weight unless otherwise indicated. Further, unless shown otherwise, all reactions, separations, distillations, and storage were carried out in a nitrogen atmosphere.

TABLE I
SUMMARY OF PREPARATION OF DIOXOLES OF FORMULA (3) AND DIOXOLANES OF FORMULA (4)

| Example No. | Compound No. | Y | Z | R |
|---|---|---|---|---|
| | Prep. of: | | | |
| 1A | (4a) | Cl | F | $CF_3$ |
| 1B | (3a) | Cl | F | $CF_3$ |
| 1B | (3b) | F | H | $CF_3$ |
| 1B | (4b) | F | H | $CF_3$ |
| 1C | (3a) | Cl | F | $CF_3$ |
| 1D | (3b) | F | H | $CF_3$ |
| 8A | (4c) | H | H | $CF_3$ |
| 8A | (4d) | Cl | H | $CF_3$ |
| 8A | (4e) | Cl | Cl | $CF_3$ |
| 8B | (3c) | H | H | $CF_3$ |
| 8B | (3d) | Cl | H | $CF_3$ |
| 8B | (3e) | Cl | Cl | $CF_3$ |
| 8C | (3d) | Cl | H | $CF_3$ |
| 15A | (4f) | Cl | F | F |
| 15B | (3f) | Cl | F | F |
| 15B | (3g) | F | H | F |
| 15B | (4g) | F | H | F |
| 16A/B | (4g) | F | H | F |
| 17 | (3g) | F | H | F |
| 22 | (4h) | H | H | F |
| 22 | (3h) | H | H | F |
| 25 | (4i) | Cl | H | F |
| 25 | (3i) | Cl | H | F |
| 28 | (3j) | Cl | Cl | F |
| 28 | (4j) | Cl | Cl | F |

TABLE II
SUMMARY OF EXAMPLES - POLYMERIZATION

| Example No. | Monomer Compound No. | Comonomer | Polymer Properties Mol % Dioxole, Tm,* Tg** |
|---|---|---|---|
| 2 | (3b) | — | 100%, Tg > 300° C. |
| 3 | (3b) | TFE | 5.2%, Tm = 266° & 320° C. |
| 4 | (3b) | TFE | 28.8%, Tg = 58° C. |
| 5 | (3b) | TFE | 2.4%, Tm = 307° C. |
| 6 | (3a) | TFE | 3.1%, Tm = 295° C. |
| 7 | (3a) | TFE/$VF_2$ | 5.3%, 14.3% TFE; Tm = 131° C. |
| 9 | (3c) | TFE | 6.9%, Tm = 253° C. |
| 10 | (3c) | TFE | 46.3%, Tg = 61° C. |
| 11 | (3c) | TFE/$VF_2$ | 7.9%, 36.4% TFE; Elast., Tm = 114° C. |
| 12 | (3c) | — | 100% |
| 13 | (3d) | TFE | 5.9%, Tm = 269° C. |
| 14 | (3c)/(3d) | TFE | 8.6% (3c)/6.2% (3d), Tg = 54° C. |
| 18 | (3g) | TFE | 4.0%, Tm = 274° C. |
| 19 | (3g) | — | 100% |
| 20 | (3f) | TFE | 10.5%, Tg = 61° C. |
| 21 | (3f) | TFE/$VF_2$ | 9.9%, 27.7% TFE; no Tm |
| 23 | (3h) | — | 100% |
| 24 | (3h) | TFE | 7% |
| 26 | (3i) | TFE | 6% |
| 27 | (3e) | TFE | 0.6%, Tm = 312° C. |
| 29 | (3j) | TFE | 1.4%, Tm = 310°, 297° C. |

*melt temperature (indicates that the polymer has crystallite regions)
**glass transition temperature (indicates that the polymer is amorphous)

EXAMPLE 1

Preparation of 2,2-bis(trifluoromethyl)-4-chloro-5-fluoro-1,3-dioxole, (3a), 2,2-bis(trifluoromethyl)-4-fluoro-1,3-dioxole, (3b), and the corresponding dioxolanes (4a) and (4b).

A. 2,2-Bis(trifluoromethyl)-4,4,5-trichloro-5-fluoro-1,3-dioxolane, (4a).

A 330 mL "Hastelloy" C lined shaker tube was charged under anhydrous conditions with 100 g (0.286 mole) of 2,2-bis(trifluoromethyl)-4,4,5,5-tetrachloro-1,3-dioxolane (4e) and 8.6 g (0.0432 mole) of antimony pentachloride; the tube was then chilled to about −50° C., and 20 g (1 mole) of hydrogen fluoride was introduced into it. The tube was mounted in a horizontal shaker, agitated for 5 hours at 70° C., then chilled in wet ice, slowly vented, and opened. The tube contents were dumped into wet ice. The liquid product was separated from the ice water, washed twice with 50 mL portions of cold water, then with 20 mL of a 10% aqueous sodium carbonate solution. There was obtained 83.5 g of a clear, colorless liquid product of which approximately 93% was the desired 2,2-bis(trifluoromethyl)-4,4,5-trichloro-5-fluoro-1,3-dioxolane, (4a).

The product was distilled at atmospheric pressure on a 0.76 m spinning band column; a small amount of 2,2-bis(trifluoromethyl)-4,5-dichloro-4,5-difluoro-1,3-dioxolane (about 2% of the product) boiling at 85°–86° C. distilled first, followed by the 2,2-bis(trifluoromethyl)-4,4,5-trichloro-5-fluoro-1,3-dioxolane, b.p. 115° C., which was obtained as a colorless, clear liquid in purity exceeding 99%. Both infrared spectroscopy and Fluorine-19 nuclear magnetic resonance spectroscopy were consistent with this chemical structure.

The pot residue was largely starting material, approximately 5% of the total mixture from the shaker tube run.

B. Dechlorination of 2,2-bis(trifluoromethyl)-4,4,5-trichloro-5-fluoro-1,3-dioxolane, (4a).

A 300 mL, 3-neck glass flask equipped with magnetic stirrer, thermometer, Vigreux column, still head to a 100 mL receiver, and dry ice trap under 100 kPa of nitrogen was charged with 165 mL of 5 1-propanol, 42.6 g (0.651 mole) of zinc dust, and 1.4 g (0.0109 mole) of zinc chloride. The mixture was stirred while being heated to 98° C. over a 21 minute period; when this temperature was reached, 2,2-bis(trifluoromethyl)-4,4,5-trichloro-5-fluoro-1,3-dioxolane, 72.0 g (0.217 mole), was introduced into the refluxing mixture via a syringe pump at 0.33 mL/minute. Thirty-five minutes later the head temperature fell to 59° C., and distillation of the product was started. Total addition time was 127 minutes. Total distillation time was 268 minutes, during which time the head temperature decreased to a minimum of 55° C. The distillate, 60 mL, contained some 1-propanol which was extracted with water, leaving 47.7 g of a clear, colorless liquid containing about 52% of 2,2-bis(trifluoromethyl)-4-chloro-5-fluoro-1,3-dioxole, (3a), 25% of 2,2-bis(trifluoromethyl)-4-fluoro-1,3-dioxole, (3b), and 22% of 2,2,-bis(trifluoromethyl)-4,5-dichloro-4-fluoro-1,3-dioxolane (4b) as a mixture of 30% cis and 70% trans isomers.

The crude reaction product was fractionated at atmospheric pressure on a 0.51 m spinning band column. 2,2-Bis(trifluoromethyl)-4-fluoro-1,3-dioxole, (3b), b.p. 44°–45° C., polymerizes spontaneously at room temperature when pure. It was therefore collected in a receiver maintained at −80° C. and stored in a dry ice chest. 2,2-Bis(trifluoromethyl)-4-chloro-5-fluoro-1,3-dioxole, (3a), distilled at 56° C.; this monomer did not polymerize spontaneously at room temperature. The cis/trans mixture of 2,2-bis(tri-fluoromethyl)-4,5-dichloro-4-fluoro-1,3-dioxolane, (4b), distilled within the range of 82°–90° C.

The IR, F-19 and proton NMR spectra, and mass spectrometry support the above chemical structures.

C. Alternate dechlorination of 2,2-bis(trifluoromethyl)-4,4,5-trichloro-5-fluoro-1,3-dioxolane, (4a).

The equipment described in the above section B was charged with 80 mL of tetrahydrofuran, 10.8 g (0.444 mole) of magnesium turnings, 0.2 g of mercuric chloride, and 0.2 g of iodine and heated to 66° C. (iodine color disappears). 2,2-Bis(trifluoromethyl)-4,4,5-trichloro-5-fluoro-1,3-dioxolane, 33.1 g (0.1 mole), was added by means of a syringe pump at the rate of 0.16 mL/minute over a period of 110 minutes. Distillation was started 41 minutes after the addition; the head temperature remained at 54°–55° C. during the remainder of the addition. The distillation was stopped after 2.5 hours, and the distillate was extracted with water to remove some tetrahydrofuran. The extracted clear, colorless liquid was found by gas chromatography to contain about 95% of 2,2-bis(trifluoromethyl)-4-chloro-5-fluoro-1,3-dioxole, (3a); the 2,2-bis(trifluoromethyl)-4-fluoro-1,3-dioxole, (3b), amounted to only 1%.

D. Alternate preparation of 2,2-bis(trifluoromethyl)-4-fluoro-1,3-dioxole, (3b).

Using the same equipment, except for a smaller, 100 mL flask, a mixture of 30 mL of tetrahydrofuran, 3.6 g of magnesium turnings, 0.2 g of mercuric chloride, and 0.1 g of iodine was heated to reflux. 2,2-Bis(trifluoromethyl)-4,5-dichloro-4-fluoro-1,3-dioxolane, (4b), 10 g, (prepared as described in Section B, above) was then introduced into the flask at approximately 0.19 mL/minute over a 34 minute period. Distillation was started 21 minutes after the addition was completed and continued until 20 mL of cold distillate was recovered. This was extracted with ice water to remove tetrahydrofuran. The remaining product was 2,2-bis(trifluoromethyl)-4-fluoro-1,3-dioxole, (3b).

EXAMPLE 2

Homopolymerization of 2,2-bis(trifluoromethyl)-4-fluoro-1,3-dioxole, (3b).

This monomer, 4.6 g, (99.88% pure by gas chromatography) was placed at 25° C. in a small, tightly capped vial under room lighting conditions. Within a few hours the viscosity of the clear liquid increased to that of a light syrup, and overnight a solid, clear, colorless plug of polymer formed on the bottom of the vial.

A small sample of the monomer-polymer syrup was evaporated on a salt plate to remove the residual monomer and form a film of the homopolymer. The infrared absorbance spectrum of this film was consistent with the molecular structure of a homopolymer of 2,2-bis(trifluoromethyl)-4-fluoro-1,3-dioxole, (3b).

The plug was placed in a vacuum oven at 110°–120° C. to remove residual monomer, and then a sample was examined by Differential Scanning Calorimetry between room temperature and 300° C. There were no second order transitions or melting points in this region, indicating that the homopolymer was amorphous and that its Tg was above 300° C.

EXAMPLE 3

Crystalline copolymer of 2,2-bis(trifluoromethyl)-4-fluoro-1,3-dioxole, (3b), and TFE.

A 110 mL stainless steel shaker tube was charged with a cold solution containing 100 g of 1,1,2-trichloro-1,2,2-trifluoroethane, 1.0 g of the dioxole, and 0.03 g of bis(4-t-butylcyclohexyl) peroxydicarbonate; the tube was chilled to −50° C. and alternately evacuated and flushed with nitrogen three times. The evacuated tube was then charged with 10 g of tetrafluoroethylene and agitated in a horizontal shaker. The temperature was held at 55° C. for two hours and then at 65° C. for two hours. After cooling the tube and venting, the resulting suspension of copolymer in 1,1,2-trichloro-1,2,2-trifluoroethane was recovered. The solvent was distilled off, and the polymer was dried to give 9.7 g of white, solid granules. A portion of these was pressed at 300° C. into a tough, self-supporting film. The infrared spectrum of the film showed absorbancies characteristic of a tetrafluoroethylene/2,2-bis(trifluoromethyl)-4-fluoro-1,3-dioxole copolymer. Differential Scanning Calorimetry showed a major, broad, crystalline melting point at 266° C.; there also was a minor melting point at 320° C. Infrared and F-19 NMR spectra support the copolymer structure containing 94.8 mole % of tetrafluoroethylene and 5.2 mole % of 2,2-bis(trifluoromethyl)-4-fluoro-1,3-dioxole, (3b).

EXAMPLE 4

Amorphous copolymer of 2,2-bis(trifluoromethyl)-4-fluoro-1,3-dioxole, (3b), and TFE.

A shaker tube was charged with 100 g of 1,1,2-trichloro-1,2,2-trifluoroethane, 0.03 g of bis(4-t-butylcyclohexyl) peroxydicarbonate, 5.0 g (0.022 mole) of the dioxole, and 5.0 g (0.05 mole) of TFE. Polymerization was carried out at 55° and 65° C. After separating and drying the product, 4.5 g of a white solid polymeric product was obtained. A portion of the product was pressed at 230° C. into thin, tough, clear, colorless, self-supporting films. The infrared and F-19 NMR spectra established the product to be a copolymer containing 71.2 mole % of TFE and 28.8 mole % of the dioxole. Differential Scanning Calorimetry showed a Tg at 58° C. but no melting point, thereby indicating that the copolymer was amorphous.

EXAMPLE 5

A high melting crystalline copolymer of 2,2-bis(trifluoromethyl)-4-fluoro-1,3-dioxole, (3b) and TFE.

A shaker tube was charged with 100 g of 1,1,2-trichloro-1,2,2-trifluoroethane, 0.03 g of bis(4-t-butylcyclohexyl) peroxydicarbonate, 0.5 g (0.0022 mole) of the dioxole, and 10 g (0.1 mole) of TFE. Polymerization was carried out at 55° and 65° C. After separating and drying the product, 9.4 g of a white, solid polymer was obtained. A portion of the polymer was pressed at 330° C. into thin, tough, colorless, transparent, self-supporting films. The infrared and F-19 NMR spectra were consistent with a copolymer of 97.6 mole % TFE and 2.4 mole % of 2,2-bis(trifluoromethyl)-4-fluoro-1,3-dioxole. Differential Scanning Calorimetry showed a relatively sharp melting point at 307° C., thus indicating the crystalline nature of the polymer.

EXAMPLE 6

A crystalline copolymer of 2,2-bis-(trifluoromethyl)-4-chloro-5-fluoro-1,3-dioxole, (3a), and TFE.

A shaker tube was charged with 100 g of 1,1,2-trichloro-1,2,2-trifluoroethane, 0.03 g of bis(4-t-butylcyclohexyl) peroxydicarbonate, 1.5 g (0.0058 mole) of the dioxole and 10 g of TFE, and polymerization was carried out at 55° and 65° C. After separating and drying the product, 4.3 g of a white, solid polymer was obtained. A portion of the polymer was pressed at 300° C. to give tough, thin, colorless, clear, self-supporting films. Infrared and F-19 NMR spectra support the structure of a copolymer containing 96.9 mole % of TFE and 3.1 mole % of 2,2-bis(trifluoromethyl)-4-chloro-5-fluoro-1,3-dioxole, (3a). Differential Scanning Calorimetry showed a melting point at 295° C., indicating the crystalline nature of the polymer.

EXAMPLE 7

A terpolymer of 2,2-bis(trifluoromethyl)-4-chloro-5-fluoro-1,3-dioxole, (3a), vinylidene fluoride, and TFE.

A shaker tube was charged with 100 g of 1,1,2-trichloro-1,2,2-trifluoroethane, 3.0 g of the dioxole, 0.03 g of bis(4-t-butylcyclohexyl) peroxydicarbonate, 6.0 g of vinylidene fluoride, and 6.0 g of TFE. Polymerization was carried out at 55° and 65° C. for 4 hours under autogenous pressure. After separating and drying the product, 3.6 g of a white, solid polymer was obtained. A portion of this polymer was pressed at 230° C. into thin, tough, clear, self-supporting films. Infrared and F-19 NMR spectra identified the polymer as a terpolymer containing 14.3 mole % of TFE, 80.4 mole % of vinylidene fluoride, and 5.3 mole % of the dioxole. Differential Scanning Calorimetry showed a melting point at 131° C., thus demonstrating the crystalline character of the polymer.

EXAMPLE 8

Preparation of 2,2-bis(trifluoromethyl)-1,3-dioxole, (3c), 2,2-bis(trifluoromethyl)-4-chloro-1,3-dioxole, (3d), and 2,2-bis(trifluoromethyl)-4,5-dichloro-1,3-dioxole, (3e).

A. Synthesis of 2,2-bis(trifluoromethyl)-4,5-dichloro-1,3-dioxolane, (4c), 2,2-bis(trifluoromethyl)-4,4,5-trichloro-1,3-dioxolane, (4d), and 2,2-bis(trifluoromethyl)-4,4,5,5-tetrachloro-1,3-dioxolane, (4e).

A 300 mL, 3-neck round bottom flask equipped with a magnetic stirrer, chlorine gas inlet, thermometer, and a water condenser topped by a dry ice condenser communicating with a drying tower and then with a water scrubber was charged with 210 g (1.0 mole) of 2,2-bis(trifluoromethyl)-1,3-dioxolane. After purging the system with nitrogen, chlorine was passed into the solution at such a rate as to maintain a yellow coloration of the solution. The stirred mixture was irradiated with a 275 watt General Electric sun lamp so as to maintain a reaction temperature for the most part in the range of 46°-72° C. for 4.5 hours. The concentration of the starting dioxolane in the reaction mixture had dropped by then to approximately 0.1%, and the reaction was terminated. Residual chlorine and hydrogen chloride were removed with a water aspirator, leaving a colorless, clear liquid weighing 289 g and containing the di-, tri-, and tetrachloro-derivatives (4c), (4d), and (4e), as confirmed by NMR, mass spectrometry, and gas chromatographic analyses.

B. Dechlorination of the di-, tri-, and tetrachlorodioxolanes obtained in step A, above.

A 500 mL, 3-neck, round bottom flask equipped with a magnetic stirrer, a syringe pump inlet, a thermometer, a 15-cm still leading to a 100 mL receiver and then to a nitrogen tee and a bubbler was charged with 98.1 g (1.5 moles) of zinc dust, 3.0 g (0.022 mole) of zinc chloride, and 300 mL of n-butyl alcohol. A syringe pump was charged with 139.5 g of the chlorinated dioxolanes from step A. After the flask contents were brought to 115° C., the chlorinated dioxolanes were pumped into the flask at 0.33 mL/minute. The addition was completed in 224 minutes. Twenty minutes after the start of the addition, distillation began at a rate of about 15-20 mL/hour. The head temperature then was 79°-80° C. but during the distillation decreased to 75° C. and at the end was 116° C.; 119.8 g of product containing butyl alcohol was distilled. The product distribution was about 21% of 2,2-bis(trifluoromethyl)-1,3-dioxole, (3c), 47% of 2,2-bis(trifluoromethyl)-4-chloro-1,3-dioxole, (3d), and 30% of 2,2-bis(trifluoromethyl)-4,5-dichloro-1,3-dioxole, (3e). The crude product was fractionated at atmospheric pressure on a 0.76 m spinning band column to provide each dioxole as a clear, colorless liquid having a purity of at least 99%: 2,2-bis(trifluoromethyl)-1,3-dioxole, (3c), b.p. 67° C.; 2,2-bis(trifluoromethyl)4-chloro-1,3-dioxole, (3d), b.p. 76° C.; and 2,2-bis(trifluoromethyl)-4,5-dichloro-1,3-dioxole, (3e), b.p. 85° C. The infrared, F-19 and proton NMR, and mass spectrometry data for these dioxoles support their molecular structures.

C. Alternate synthesis of 2,2-bis(trifluoromethyl)-4-chloro-1,3-dioxole, (3d).

A 100 mL, 2-neck, round-bottom glass flask equipped with magnetic stirrer, thermometer, Vigreux column, still head, and receiver was charged under a nitrogen blanket with 40 mL of di(ethylene glycol) dimethyl ether, 9.8 g of crude 2,2-bis(trifluoromethyl)-4,5-dichloro-1,3-dioxolane, (4c), and 6.7 g of solid potassium hydroxide. The flask contents were heated at 141° C. for 2 hours during which time the 2,2-bis(trifluoromethyl)-4-chloro-1,3-dioxole, (3d), distilled over. Purified by gas chromatography, the product had the same retention time and infrared spectrum as an authentic sample of 2,2-bis(trifluoromethyl)-4-chloro-1,3-dioxole, (3d).

EXAMPLE 9

A crystalline copolymer of 2,2-bis(trifluoromethyl)-1,3-dioxole, (3c) and TFE.

A shaker tube was charged with 100 g of 1,1,2-trichloro-1,2,2-trifluoroethane, 0.03 g of bis(4-t-butylcyclohexyl) peroxydicarbonate, 1.5 g (0.0072 mole) of the dioxole, and 10 g (0.1 mole) of TFE. Polymerization was carried out at 55° and 65° C. After separating and drying the product, 10.5 g of a white, solid polymer was obtained. A portion of the polymer was pressed at 300° C. into tough, clear, colorless, self-supporting films. Infrared and F-19 NMR spectra established a copolymer structure of 93.1 mole % of TFE and 6.9 mole % of 2,2-bis(trifluoromethyl)-1,3-dioxole, (3c). Differential Scanning Calorimetry showed a melting point at 253° C., thereby establishing the crystalline character of this polymer.

EXAMPLE 10

An amorphous copolymer of 2,2-bis(trifluoromethyl)-1,3-dioxole, (3c) and TFE.

A shaker tube was charged with 100 g of 1,1,2-trichloro-1,2,2-trifluoroethane, 4.2 g (0.02 mole) of the dioxole, 0.03 g of bis(4-t-butylcyclohexyl) peroxydicarbonate, and 10 g of TFE. Polymerization was carried out at 55° and 65° C. under autogenous pressure for 4 hours. After separation and drying, a white, solid polymer, 1.4 g, was obtained. It was soluble in the trichlorotrifluoroethane solvent; a clear, transparent, self-supporting film was cast from this solution. Infrared and F-19 and proton NMR spectra identified the copolymer as containing 46.3 mole % of the dioxole and 53.7 mole % of TFE. Differential Scanning Calorimetry showed a Tg at 61° C. and other transitions at 113° C. and 246° C.; there was no melting point, and the polymer was therefore amorphous.

EXAMPLE 11

An elastomeric terpolymer of 2,2-bis(trifluoromethyl)-1,3-dioxole, (3c), vinylidene fluoride, and TFE.

A shaker tube was charged with 100 g of 1,1,2-trichloro-1-2,2,-trifluoroethane, 3.0 g (0.0144 mole) of the dioxole, 0.03 g of bis(4-t-butylcyclohexyl) peroxydicarbonate, 6.0 g (0.094 mole) of vinylidene fluoride, and 6.0 g (0.06 mole) of TFE. Polymerization was carried out under autogenous pressure at 55° and 65° C. After separation and drying, a white, solid polymer, 6.4 g, was obtained. It was not soluble in the trichlorotrifluoroethane. A portion of the polymer was pressed at 230° C. to give thin, tough, elastomeric, clear, self-supporting films. Infrared and F-19 NMR spectra identified the terpolymer as containing 36.4 mole % of TFE, 55.7 mole % of vinylidene fluoride, and 7.9 mole % of dioxole. Differential Scanning Calorimetry showed a melting point at 114° C., indicating the crystalline nature of the polymer.

EXAMPLE 12

Homopolymer of 2,2-bis(trifluoromethyl)-1,3-dioxole, (3c).

The dioxole, 3.0 g, which had been kept in a dry ice chest, was placed in a 10 mL closely capped, clear, glass vial and allowed to stand at room temperature under laboratory fluorescent lighting conditions. After two weeks, a portion of the liquid was placed on a salt plate and allowed to evaporate, leaving a thin, transparent, clear, colorless solid film. Infrared analysis of this film was consistent with the homopolymer structure.

EXAMPLE 13

A crystalline copolymer of TFE and 2,2-bis(trifluoromethyl)-4-chloro-1,3-dioxole, (3d).

A shaker tube was charged with 100 g of 1,1,2-trichloro,1,2,2-trifluoroethane, 0.03 g of bis (4-t-butylcyclohexyl) peroxydicarbonate, 1.5 g (0.00618 mole) of the dioxole, and 10 g (0.1 mole) of TFE. Polymerization was carried out under autogenous pressure at 55° and 65° C. After separation and drying, a white solid polymer, 5.0 g, was obtained. A portion of the polymer was pressed at 300° C. into thin, tough, clear, self-supporting films. Infrared and F-19 NMR spectra showed the copolymer to contain 94.1 mole % of TFE and 5.9 mole % of the dioxole. Differential Scanning Calorimetry showed a melting point at 269° C., thus indicating the polymer to be crystalline.

EXAMPLE 14

An amorphous terpolymer of TFE with 2,2-bis(trifluoromethyl)-1,3-dioxole, (3c) and 2,2-bis(trifluoromethyl)-4-chloro-1,3-dioxole, (3d).

A shaker tube was charged with 100 g of 1,1,2-trichloro-1,2,2-trifluoroethane, 1.0 g of 2,2-bis(trifluoromethyl)-1,3-dioxole, (3c), 2.0 g of 2,2-bis(trifluoromethyl)-4-chloro-1,3-dioxole, (3d) 0.03 g of bis(4-t-butylcyclohexyl) peroxydicarbonate, and 10 g TFE. Polymerization was carried out under autogenous pressure at 55° and 65° C. After separation and drying, 3 g of white, solid, polymer granules were obtained. A portion of the polymer was pressed at 300° C. to give thin, tough, self-supporting, colorless, clear films. The infrared and F-19 NMR spectra were consistent with a terpolymer structure consisting of 85.2 mole % of TFE, 8.6% of 2,2-bis(trifluoromethyl)-1,3-dioxole, (3c), and 6.2 mole % of 2,2-bis(trifluoromethyl)-4-chloro-1,3-dioxole, (3d). The Differential Scanning Calorimetry analysis showed a Tg at 54° C. but no melting point, thereby indicating the polymer to be amorphous.

EXAMPLE 15

Preparation of 2,2,4-trifluoro-5-chloro-1,3-dioxole, (3f) 2,2,4-trifluoro-1,3-dioxole, (3g), and the corresponding dioxolanes (4f) and (4g). A. 2,2,4-trifluoro-4,5,5-trichloro-1,3-dioxolane (4f).

A dry, 360 mL "Hastelloy" C lined shaker tube was charged with 81.8 g (0.33 mole) of 2,2-difluoro-4,4,5,5-tetrachloro-1,3-dioxolane, (4j), containing 9.0 g (0.03 mole) of antimony pentachloride. The tube was cooled, alternately evacuated and purged with nitrogen three times, and charged with 22 g (1.1 mole) of hydrogen fluoride. The tube was agitated and warmed to 40° C. over a period of 1 hour, heated under autogenous pressure for 4 hours at 40° C., then cooled to 0° C., slowly vented, and opened. The contents were poured into ice; the organic phase was separated from the aqueous phase, extracted twice with distilled water and once with an aqueous 10% sodium carbonate solution; 63.3 g of crude product was obtained which contained about 3.9% of 2,2,4,5-tetrafluoro-4,5-dichloro-1,3-dioxolane, 85.8% 2,2,4-trifluoro-4,5,5-trichloro-1,3-dioxolane, (4f), and 8.1% of the starting material. This product mixture was combined with those of three other similar runs and separated by distillation on a 0.76 m spinning band column; 2,2,4,5-tetrafluoro-4,5-dichloro-1,3-dioxolane boiled at 45°–46° C.; 2,2,4-trifluoro-4,5,5-trichloro-1,3-dioxolane, (4f), at 84° C.; and the starting material, 2,2-difluoro-4,4,5,5-tetrachloro-1,3-dioxolane (4j), at 115° C. Their purities were greater than 99%. Both infrared and F-19 NMR spectroscopy confirmed their structures. B. Dechlorination of 2,2,4-trifluoro-4,5,5-trichloro-1,3-dioxolane, (4f).

A 300 mL 3-neck glass flask equipped with magnetic stirrer, thermometer, Vigreux column with a dry ice-cooled still head leading to a cold receiver, trap, a nitrogen tee, and bubbler was charged with 76.7 g (1.17 gram-atoms) of zinc, 2.6 g (0.019 mole) of zinc chloride, and 175 mL of propanol. The stirred mixture was heated to 94° C.; then 89.6 g (0.387 mole) of 2,2,4-trifluoro-4,5,5-trichloro-1,3-dioxolane, (4f), was introduced from a syringe pump at a rate of 0.33 mL/minute during 172 minutes. Distillation at a rate of about 15 mL/hour began 33 minutes after the start of the addition and continued for 270 minutes; 65 mL of clear, colorless distillate weighing 84.5 g and containing some propanol was obtained. It was redistilled through a 0.76 m spinning band column with a dry ice-cooled head. The product distribution was approximately 3.9% of 2,2,4-trifluoro-1,3-dioxole, (3g), b.p. 10° C.; 71.7% of 2,2,4-trifluoro-5-chloro-1,3-dioxole, (3f), b.p. 25°–27° C.; and 24.3% of 2,2,4-trifluoro-4,5-dichloro-1,3-dioxolane, (4g), b.p. 73° C. The infrared, F-19 and proton NMR spectra of these compounds were consistent with the assigned structures.

EXAMPLE 16

Alternate synthesis of 2,2,4-trifluoro-4,5-dichloro-1,3-dioxolane, (4g). A. 4,4,5-trichloro-1,3-dioxolan-2-one.

A creased 3-neck, 300 mL, round bottom flask equipped with magnetic stirrer, gas inlet tube, thermometer, and water condenser topped by a dry ice condenser leading to a trap and scrubber was charged with 88.1 g of ethylene carbonate. The system was purged with nitrogen and then dry chlorine gas was introduced while irradiating the reaction vessel with a 275 watt General Electric Sun Lamp; the amount of chlorine was sufficient to maintain a yellow color in the solution. The temperature ranged from 35° C. during the initial part of the chlorination and up to 115° C. during the later part of the 6-hour reaction. The reaction mixture was analyzed by gas chromatography techniques and, when all of the 4-chloro-1,3-dioxolan-2-one had been consumed, the reaction was terminated. The product was principally 4,4,5-trichloro-1,3-dioxolan-2-one with lesser amounts of 4,5-dichloro- and 4,4,5,5-tetrachloro-derivatives. Two similar runs were made and the products combined. B. Fluorination of 4,4,5-trichloro-1,3-dioxolan-2-one.

A shaker tube was charged with 113 g of crude 4,4,5-trichloro-1,3-dioxolan-2-one, 18 g of HF, and 194 g of SF$_4$. After agitating 10 hours at 200° C., the tube was cooled to 0° C., and the product was mixed with ice. The organic phase was separated and neutralized by shaking with an aqueous potassium carbonate solution and then distilled on a 0.76 m spinning band column; the first fraction, 2,2,4,5-tetrafluoro-4,5-dichloro-1,3-dioxolane, b.p. 47°–48° C., was followed by the desired 2,2,4-trifluoro-4,5-dichloro-1,3-dioxolane, (4g), b.p. 69°–73° C. Infrared and F-19 NMR spectra were consistent with this structure.

EXAMPLE 17

Preparation of 2,2,4-trifluoro-1,3-dioxole, (3g), by dechlorination of 2,2,4-trifluoro-4,5-dichloro-1,3-dioxolane, (4g).

A 100 mL, 3-neck, round bottom flask equipped with magnetic stirrer, thermometer, Vigreux still leading to a dry ice-cooled head, cold receiver and trap, was charged under a nitrogen blanket with 3.6 g of magnesium turnings, 0.2 g of mercuric chloride, 0.1 g of iodine, and 30 mL of tetrahydrofuran. The mixture was stirred and heated to 67° C.; 8.8 g of 2,2,4-trifluoro-4,5-dichloro-1,3-dioxolane, (4g), was then added at a rate of 0.092 mL/minute. After 2.2 mL had been added the distillation began and continued for 3 hours until 5 mL of distillate was obtained. The cold distillate was extracted with ice water to remove some tetrahydrofuran and there remained 4.7 g of product which was largely 2,2,4-trifluoro-1,3-dioxole, (3g), b.p. 10° C.

This dioxole was purified by gas chromatography; the infrared absorbance spectra, and especially the absorbance in the region of 5.6 μm, as well as its subsequent polymerization substantiated the assigned molecular structure.

EXAMPLE 18

A crystalline copolymer of tetrafluoroethylene with 2,2,4-trifluoro-1,3-dioxole, (3g).

A shaker tube was charged with 100 g of 1,1,2-trichloro-1,2,2-trifluoroethane, 0.8 g of the dioxole, 0.03 g of bis(4-t-butylcyclohexyl) peroxydicarbonate, and 10 g of TFE and heated at 55° and 65° C. for 4 hours. After separation of the product and drying, 4.7 g of a white solid polymer was obtained. A portion of this was pressed at 330° C. to give thin, tough, self-supporting, colorless films. The infrared and F-19 NMR spectra showed the copolymer composition to be 96.0 mole % TFE and 4.0 mole % dioxole. Differential Scanning Calorimetry showed a crystalline melting point at 274° C.

EXAMPLE 19

Homopolymer of 2,2,4-trifluoro-1,3-dioxole, (3g).

A 10 mL clear, glass vial was charged with 5.7 g of 1,1,2-trichloro-1,2,2-trifluoroethane, 0.001 g of bis(4-t-butylcyclohexyl) peroxydicarbonate, and 0.5 g of the dioxole, capped securely and allowed to stand two days on the bench top at about 25° C. exposed to the normal fluorescent light of the laboratory. A portion of the solution was then evaporated on a micro salt plate to give a clear, colorless, self supporting film which was identified by its infrared spectrum to be the dioxole homopolymer.

EXAMPLE 20

An amorphous copolymer of TFE and 2,2,4-trifluoro-5-chloro-1,3-dioxole, (3f).

A shaker tube was charged with 100 g of 1,1,2-trifluoro-1,2,2-trichloroethane, 1.7 g of the dioxole, 0.03 g of bis(4-t-butylcyclohexyl) peroxydicarbonate, and 10 g of TFE. Polymerization was carried out at 55° and 65° C. under autogenous pressure for 4 hours. After separation and drying of the product, 1.8 g of a white, solid polymer was obtained. A portion of this was pressed at 300° C. to give thin, tough, self-supporting, colorless clear films. The infrared and F-19 NMR spectra of this polymer showed it to contain 10.5 mole % of the dioxole and 89.5 mole % of TFE. Differential Scanning Calorimetry showed a Tg of 61° C.; there was no melting point.

EXAMPLE 21

An amorphous, elastomeric terpolymer of TFE, 2,2,4-trifluoro-5-chloro-1,3-dioxole, (3f), and vinylidene fluoride.

A shaker tube was charged with 100 g of 1,1,2-trichloro-1,2,2-trifluoroethane, 2.1 g of the dioxole, 0.03 g of bis(4-t-butylcyclohexyl) peroxydicarbonate, 6 g of vinylidene fluoride, and 6 g of TFE. Polymerization was carried out at 55° and 65° C. over a 4 hour period under autogenous pressure. After separating and drying, there was obtained 2.5 g of white, solid polymer granules. A portion of this polymer was pressed at 200° C. to give thin, elastic, tough, self supporting, clear, colorless films. Infrared and F-19 NMR spectra showed the terpolymer to consist of 27.7 mole % of TFE, 9.9 mole % of the dioxole and 62.4 mole % of vinylidene fluoride. Differential Scanning Calorimetry showed no melting point, thus indicating an amorphous polymer.

EXAMPLE 22

Synthesis of 2,2-difluoro-1,3-dioxole, (3h)

A. 4,5-Dichloro-1,3-dioxolan-2-one

A 500 mL, 3-neck round-bottom flask equipped with a nitrogen purge line, magnetic stirrer, thermometer, and reflux condenser leading to a trap and drying tower was charged with 88 g of ethylene carbonate, 297 g of sulfuryl chloride, and 1.0 g of azobisisobutyronitrile. After purging the assembly with nitrogen, the stirred mixture was irradiated with a Hanovia mercury vapor lamp at a temperature of 34°–47° C. during the first 3 hours of the reaction. During the next 7 hours, the temperature was increased from 51° to 103° C. During the final 3 hours of the reaction, the temperature was held in the 95°–107° C. range.

After cooling to room temperature, the flask was evacuated on a water aspirator to remove small amounts of HCl. The flask contents were then flash-distilled at a pressure of about 266 Pa and a pot temperature of up to 150° C.; 85.7 g of distillate was collected. GC analysis of the distillate showed it to contain approximately 86.3% of 4,5-dichloro-1,3-dioxolan-2-one, 8.8% of 4-chloro-1,3-dioxolan-2-one, and 3.1% of 4,4,5-trichloro-1,3-dioxolan-2-one.

B. 2,2-Difluoro-4,5-dichloro-1,3-dioxolane (4h)

A 300 mL "Hastelloy" C shaker tube was charged with 136.2 g of 4,5-dichloro-1,3-dioxolan-2-one, 16.2 g of HF, and 194.4 g of SF$_4$. The tube was then heated to 150° C. and agitated for 300 hours. After the tube was cooled to 0° C., it was slowly vented and then its contents were dumped into ice. The organic layer was separated and extracted twice with 50 mL of distilled water. The product weighed 93.0 g and contained about 69% of 2,2,4-trifluoro-5-chloro-1,3-dioxolane and about 7% of 2,2-difluoro-4,5-dichloro-1,3-dioxolane, (4h).

C. Dechlorination of 2,2-difluoro-4,5-dichloro-1,3-dioxolane (4h)

Equipment like that of Example 15B, except that a 100 mL flask was used, was charged with 7.8 g of zinc dust, 0.2 g of zinc chloride, and 40 mL of butyl alcohol. The stirred mixture was heated to 114° C.; 6.5 g of crude 2,2-difluoro-4,5-dichloro-1,3-dioxolane (4h) was then added by a syringe pump at 0.092 mL/minute over a 52-minute period. Distillation began 20 minutes after the beginning of the addition and continued for 94 minutes until 4.5 mL of distillate containing some butyl alcohol was obtained. The distillate was purified by gas chromatography. The infrared absorbance spectrum, especially the absorbance in the region of 6.05 μm, was consistent with the 2,2-difluoro-1,3-dioxole structure (3h).

EXAMPLE 23

Homopolymer of 2,2-difluoro-1,3-dioxole, (3h).

A shaker tube is charged with 3 g of 2,2-difluoro-1,3-dioxole in 100 g of 1,1,2-trichloro-1,2,2-trifluoroethane, and 0.005 g of bis(4-t-butylcyclohexyl) peroxydicarbonate. Polymerization is carried out at 55° and 65° C. for 4 hours. After separating and drying the solid, white polymer, 0.6 g, a portion of it is pressed at 250° C. to give a tough, clear, transparent, self supporting, thin film, of the homopolymer, which is amorphous.

EXAMPLE 24

A crystalline copolymer of tetrafluoroethylene and 2,2-difluoro-1,3-dioxole, (3h).

A shaker tube is charged with 1 g of the dioxole in 100 g of 1,1,2-trichloro-1,2,2-trifluoroethane, 0.03 g of bis(4-t-butylcyclohexyl) peroxydicarbonate, and 10 g of TFE. Polymerization is carried out at 55° and 65° C. After separating and drying the product, 9.9 g of white, granular, solid, crystalline polymer is obtained. It contains approximately 93 mole % TFE and 7 mole % of the dioxole.

EXAMPLE 25

Synthesis of 2,2-difluoro-4-chloro-1,3-dioxole, (3i).

This synthesis is carried out in the same manner as that of Example 22, except that 106.7 g (0.5 mole) of 2,2-difluoro-4,4,5-trichloro-1,3-dioxolane, (4i), prepared from 4,4,5-trichloro-1,3-dioxolan-2-one (Example 16A) is the starting material. Rectification of the product mix through a 0.76 m spinning band column gives 47.1 g of 2,2-difluoro-4-chloro-1,3-dioxole, (3i).

EXAMPLE 26

A crystalline copolymer of TFE with 2,2-difluoro-4-chloro-1,3-dioxole, (3i).

A shaker tube is charged with 100 g of 1,1,2-trichloro-1,2,2-trifluoroethane containing 1 g of 2,2-difluoro-4-chloro-1,3-dioxole, (3i), 0.03 g of bis(4-t-butylcyclohexyl) peroxydicarbonate, and 10 g of TFE. Polymerization is carried out at 55° and 65° C. After separating and drying the product, 5.2 g of a white solid granular polymer is obtained. This is pressed at 300° C. into a tough, self-supporting, clear film. The polymer is crystalline and contains approximately 94 mole % TFE and 6 mole % of the dioxole.

EXAMPLE 27

A Crystalline TFE/2,2-bis(trifluoromethyl)-4,5-dichloro-1,3-dioxole, (3e), copolymer A 110 mL shaker tube was charged with 100 g of 1,1,2-trichloro-1,2,2-trifluoroethane, 3.0 g of the dioxole, 0.04 g bis(4-t-butylcyclohexyl) peroxydicarbonate, 10 g of TFE and heated 3.5 hours at 55° and 65° C. under autogenous pressure. After separation and drying the product, 4.3 g of a white solid polymer was obtained. Differential thermal analysis showed a crystalline melting point at 312° C.; the infrared spectrum of a film possessed the absorbancies characteristic of the TFE/2,2-bis(trifluoromethyl)-4,5-dichloro-1,3-dioxole copolymer. By elemental analysis, the copolymer contained 0.44% chlorine which corresponds to 0.6 mole percent of dioxole.

EXAMPLE 28

Synthesis of 2,2-difluoro-4,5-dichloro-1,3-dioxole, (3j)

A. Tetrachloroethylene Carbonate

A 1000 mL creased flask equipped with a stirrer, thermometer and gas inlet tube, and topped by water and dry ice condensers, was charged with 352.4 g (4 moles) of melted ethylene carbonate. The system was purged with nitrogen while ethylene carbonate was stirred and heated to 50° C. After turning off the nitrogen, chlorine was introduced at a rapid rate and when the solution turned yellow, a sunlamp was lit. The flow of chlorine and the intensity of the light were adjusted so that the solution remained yellow and the temperature did not exceed 80° C. during the first few hours of the chlorination. Later on, the temperature was increased to 100°-120° C.

The chlorination was continued until intermediates were no longer present in the product, as evidenced by periodic gas chromatographic analysis. When the product was free of the mono-, di-, and trichloro intermediates, it was distilled at a reduced pressure on a water aspirator. After the removal of chlorine and hydrogen chloride, the distillation was continued using a high vacuum pump.

B. 2,2-difluoro-4,4,5,5-tetrachloro-1,3-dioxolane (4j)

A 360 mL "Hastelloy" C shaker tube was charged with 113 g (0.5 mole) of tetrachloroethylene carbonate, closed under nitrogen, cooled in dry ice/acetone, evacuated, flushed with nitrogen, reevacuated and then charged with 18 g (0.9 mole) of HF and 194 g (1.8 mole) of SF$_4$. The tube was then agitated for 10 hours at 200° C. Following this, the tube was chilled in an ice-water bath and then slowly vented to remove the excess of SF$_4$ and HF. The product was dumped from the tube into wet ice and allowed to stand a day. The water-product mixture was placed in a polyethylene separatory funnel, and the dioxolane (4j) was withdrawn into a polyethylene Erlenmeyer flask, weighed, and stirred one hour with 10 mL of a 30% K$_2$CO$_3$ solution in water (the pH of the aqueous phase must be alkaline). The dioxolane (4j) was then separated and bottled. The 2,2-difluoro-4,4,5,5-tetrachloro-1,3-dioxolane (4j) was dried over K$_2$CO$_3$ and distilled at a reduced pressure prior to use (b.p. 126° C. at 101 KPa). F19 NMR and IR analyses supported the molecular structure.

C. Dechlorination of 2,2-difluoro-4,4,5,5-tetrachloro-1,3-dioxolane, (4j)

A 300 mL, 3-neck glass flask equipped with magnetic stirrer, thermometer, Vigreux column with a water condenser to receiver, trap to a nitrogen tee and bubbler was charged with 1-propanol, 175 mL; zinc dust, 59.3 g; zinc chloride, 2.0 g. After heating to reflux, the 2,2-difluoro-4,4,5,5-tetrachloro-1,3-dioxolane (4j), 74.3 g, was added by syringe pump at 0.33 mL/minute. The addition was complete in 148 minutes. Distillation was begun 40 minutes after the start of the addition and continued for 6 hours until 72 mL of distillate was collected. The product was 98.7% pure desired dioxole, (3j), at 100% conversion of the dioxolane; the distillate which contained some propanol was redistilled through a 0.51 m spinning band column to separate the dioxole, (3j), b.p. 64°-65° C., at a purity of 98.6%. A 3.66 m x 0.0064 m diameter 30% "Krytox" perfluoroether (Du Pont Co.) column at 60° C. was used in the analysis. The infrared spectrum was consistent with the structure.

EXAMPLE 29

A crystalline TFE/2,2-difluoro-4,5-dichloro-1,3-dioxole, (3j), copolymer.

A 110 mL shaker tube was charged with 100 g of 1,1,2-trichloro-1,2,2-trifluoroethane, 1.8 g of the dioxole, 0.04 g of bis(4-t-butylcyclohexyl) peroxydicarbonate, and 10 g of tetrafluoroethylene and heated 4 hours at 60°-65° C. After separation of the insoluble product and drying, 2.4 g of a white solid polymer was obtained. Differential Scanning Calorimetry showed a major crystalline melting point at 310° C. and a minor one at 297° C. F-19 NMR analysis showed the copolymer to contain 1.4 mole % of the dioxole (3j). Both the infrared and F-19 NMR spectra agreed with the copolymer structure.

I claim:

1. A polymer of a fluorodioxole having the formula

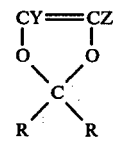

wherein Y is hydrogen or chlorine; Z is hydrogen, fluorine, or chlorine, or R is fluorine or the trifluoromethyl group; said polymer being a homopolymer, a copolymer with tetrafluoroethylene, or a terpolymer with tetrafluoroethylene and vinylidene fluoride; with the proviso that when at least one of Y and Z is chlorine, the polymer is not a homopolymer.

2. A crystalline copolymer of a fluorodioxole of claim 1 with tetrafluoroethylene.

3. A copolymer of claim 2 wherein Y is hydrogen; Z is hydrogen or fluorine: and R is trifluoromethyl.

4. An amorphous copolymer of a fluorodioxole of claim 1 with tetrafluoroethylene, wherein only one of Y and Z can be chlorine.

5. A copolymer of claim 4 wherein each of Y and Z is hydrogen, and R is trifluoromethyl.

6. A copolymer of claim 4 wherein each of Y and Z hydrogen and R is fluorine.

7. A terpolymer of a fluorodioxole of claim 1 with vinylidene fluoride and tetrafluoroethylene.

8. An amorphous homopolymer of a fluorodioxole of claim 1 in which Y is hydrogen and Z is hydrogen or fluorine.

9. A self-supporting film of a polymer of any one of claims 1-8.

* * * * *